US00PP08780P

United States Patent [19]

Bartels

[11] Patent Number: Plant 8,780

[45] Date of Patent: Jun. 14, 1994

[54] ASTER PLANT NAMED PINK CASINO

[75] Inventor: G. B. H. Bartels, Aalsmeer, Netherlands

[73] Assignee: Bartels Stek (Mr. G. b. H. Bartels), Aalsmeer, Netherlands

[21] Appl. No.: 86,142

[22] Filed: Jul. 6, 1993

[51] Int. Cl.[5] ..... A01H 5/00

[52] U.S. Cl. ..... Plt./68.1

[58] Field of Search ..... Plt. 68.1

*Primary Examiner*—James R. Feyrer

*Attorney, Agent, or Firm*—G. B. H. Bartels

[57] ABSTRACT

A distinct cultivar of aster plant named Pink Casino, characterized by its large inflorescences, fast flowering and rapid growth rate, tapering flower arrangement, and good postharvest longevity.

1 Drawing Sheet

The present invention relates to a new and distinctive cultivar of Aster hybrid, hereinafter referred to by the cultivar name Pink Casino.

The new cultivar was developed by me at Bartelstek, Aalsmeer, Holland, through controlled breeding by crossing the cultivar identified as 89-287 pink as the female parent with the cultivar identified as 89-273 white as the male parent. Both parents are hybrids of aster cultivars, species unknown.

Asexual reproduction of the new cultivar by terminal or stem cuttings taken at Aalsmeer, Holland, has shown that the unique features of this new aster are stabilized and are reproduced true to type in successive generations of asexual reproduction.

The following characteristics distinguish the new aster from both its parent varieties and other cultivated asters of this type known and used in the floriculture industry:

1. Pink Casino has large inflorescences which is distinct compared to other aster cultivars.

2. Pink Casino is vigorous with fast flowering and rapid growth rates.

3. The flower arrangement on Pink Casino is more tapering than other aster cultivars.

4. Cut flowering stems Pink Casino consistently demonstrate good longevity, generally lasting 14 days after harvesting.

The accompanying colored photographs illustrate the overall appearance and flower color of the new cultivar, showing the colors as true as it is reasonably possible to obtain in colored reproductions of this type. The photograph is a single flowering stem of Pink Casino.

The new cultivar can be compared in certain characteristics to the nonpatented cultivar Monte Casino. In general comparison to Monte Casino, Pink Casino has:

1. A larger inflorescence diameter, on average 1.5 times larger than Monte Casino.

2. Earlier flowering, usually seven to ten days earlier than Monte Casino.

3. A more tapering flower arrangement compared to Monte Casino's broader and more open flower arrangement.

4. Cut flower stems that last an average of two days longer after harvest compared to cut stems of Monte Casino.

The following is a detailed description of my new cultivar based on plants produced under normal commercial practice in Aalsmeer, Holland, in a glass-covered greenhouse with day temperatures of 16° to 18° C.

and night temperatures of 12° C. during the vegetative phase and day temperature of 22° to 25° C. and night temperatures of 18° C. during the flowering phase.

Color references are made to The Royal Horticultural Society Colour Chart except where general terms of ordinary dictionary significance are used.

Botanical classification: Aster hybrid cv Pink Casino.

Parentage:

*Male parent.*—Bartelstek 89-273 white.

*Female parent.*—Bartelstek 89-287 pink.

Propagation:

A. *Type.*—By terminal tip cuttings, tissue culture and division

B. *Time to initiate roots.*—14 days at 25° C. during the summer

C. *Time to initiate roots.*—20 days at 20° C. during the winter

D. *Rooting habit.*—Fibrous, branching

Plant description:

A. *General appearance.*—Upright and tapering, freely branching, and vigorous

B. *Foliage description.*—Shape: Linear, elongated, narrow. Size: 7.5 cm in length, 0.25 cm in width. Texture: Smooth, not pubescent. Margin: Entire. Color: Young foliage top side: 147A. Young foliage under side: 147A. Mature foliage top side: 147A. Mature foliage under side: 147A. Venation: Parallel, branched, color is 147A.

Flowering description:

A. *Flowering habit.*—Panicles of florets, radiate capitula

B. *Natural flowering season.*—Natural flowering season is the fall in the northern hemisphere C. *Quantity of flowers.*—More than ten inflorescences on each lower flowering lateral stem and more than 150 inflorescences per each harvested stem D. *Ray florets:*—Shape: Ligulate. Color: Top side: 75D. When opening: 75D. Fading to: 75D. Under side: 75D. Number of ray florets: Double rows, 25 to 30 ray florets per inflorescence. Size of inflorescence: 2.5 cm in diameter.

E. *Disc florets.—Shape: Tubular. Color: Color mature:* 6A. Color immature: 6C. Number of disc florets: 25 to 30 disc florets per inflorescence. Diameter of disc: 0.5 cm.

F. *Reproductive organs.*—Stamens: Anther color: 4D. Pollen color: 4D. Pistils: Stigma color: 6D. Style color: 144C.

Disease resistance: No fungal or bacterial problems observed to date.

I claim:

1. A new and distinct cultivar of aster plant named Pink Casino, as illustrated and described.

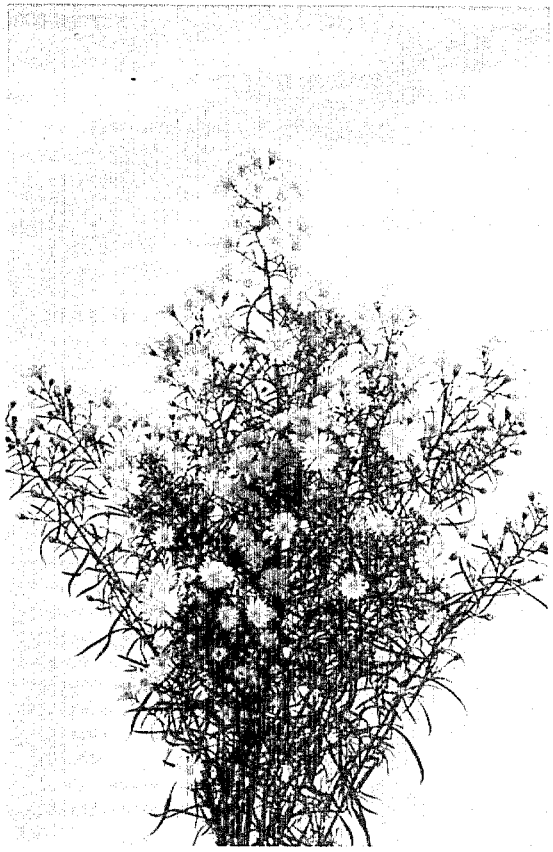

* * * * *